Figure 1:
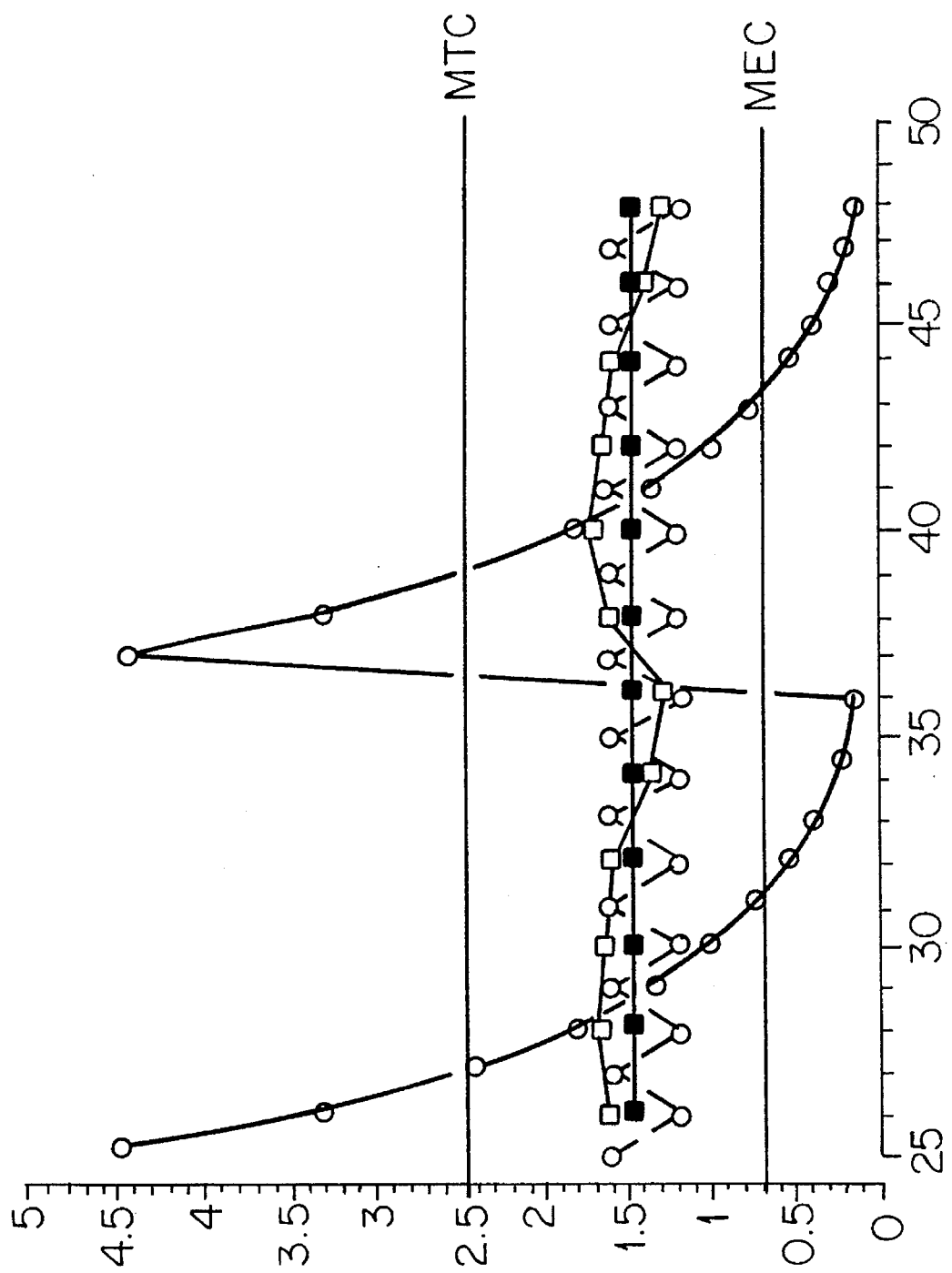

United States Patent [19]
Racz et al.

[11] Patent Number: 5,484,776
[45] Date of Patent: Jan. 16, 1996

[54] PROCESS FOR THE PRODUCTION OF STABLE LIQUID FORM OF BETA-BLOCKER-CONTAINING MEDICAMENTS WITH CONTROLLED RELEASE OF THE ACTIVE CONSTITUENT FOR ORAL ADMINISTRATION

[75] Inventors: Istvan Racz; Sylvia Marton, both of Budapest, Hungary

[73] Assignee: Synepos Aktiengesellschaft, Vaduz, Liechtenstein

[21] Appl. No.: 135,992

[22] Filed: Oct. 14, 1993

[51] Int. Cl.$^6$ .......................... A61K 9/08; A61K 31/40; A61K 47/26; A61K 31/135

[52] U.S. Cl. ................. 514/54; 514/58; 514/59; 514/782; 514/965

[58] Field of Search .................. 514/58, 54, 59, 514/782, 965

[56] References Cited

U.S. PATENT DOCUMENTS

| | | | |
|---|---|---|---|
| 3,341,584 | 9/1967 | Larsen et al. | 562/478 |
| 4,198,526 | 4/1980 | Edwards | 562/478 |
| 4,248,858 | 2/1981 | Guley et al. | 424/438 |
| 4,309,405 | 1/1982 | Guley et al. | 424/438 |
| 4,428,883 | 1/1984 | Hussain | 562/478 |
| 4,689,235 | 8/1987 | Barnes et al. | 426/89 |
| 4,834,985 | 5/1989 | Elger et al. | 424/488 |
| 4,885,293 | 12/1989 | Andrews et al. | 514/913 |
| 4,915,949 | 4/1990 | Wong et al. | 424/438 |
| 5,100,688 | 3/1992 | Cox et al. | 426/573 |
| 5,102,546 | 6/1992 | Hansen et al. | 424/448 |
| 5,225,219 | 7/1993 | Inglett | 426/46 |

*Primary Examiner*—Ronald W. Griffin
*Attorney, Agent, or Firm*—Finnegan, Henderson, Farabow, Garrett & Dunner

[57] ABSTRACT

This invention relates to a process for the production of optimally stable orally administrable solution forms of medicaments containing high-molecular polysaccharides, with controlled release of drugs having beta-blocking action, this process consisting of the reacting of 1 to 20 parts (w/w) of beta-blocking agent (oxprenolol, pindolol, sotalol, metoprolol, alprenolol, acebutolol, atenolol, bopindolol, practolol, nadolol or propranolol) in 100 parts of an aqueous solution with 0.001 to 10.0 parts of a polysaccharide polymer, advantageously with Xanthan Gum having beta-1,4-glucan chain, or dextran, or amylodextrin, or carboxymethylamylum. The reaction is allowed to take place in the course of 20 minutes at a pH adjusted no 2.0–4.5, with vigorous stirring at 80° C. temperature. Following the usual method of the pharmaceutical practice, the system is then formulated by the addition of water to obtain a solution suitable for oral administration.

25 Claims, 3 Drawing Sheets

PROCESS FOR THE PRODUCTION OF STABLE LIQUID FORM OF BETA-BLOCKER-CONTAINING MEDICAMENTS WITH CONTROLLED RELEASE OF THE ACTIVE CONSTITUENT FOR ORAL ADMINISTRATION

This invention relates to a process for the preparation of optimally stable, orally administered solution forms of medicaments containing polysaccharides ensuring controlled release of the active ingredient, which is a beta-adrenergic receptor blocking agent.

In recent years, the use of beta-adrenergic receptor inhibitors has resulted in considerable therapeutic success in the treatment of arrhythmia and circulatory disorders (hyperkinesis, angina pectoris, hypertension, etc.).

Up to now, however, the physician has had at his disposal only very few dosage forms for such a treatment, in general, only tablets and injections. It is perfectly evident that the real and proper solution would be the clinical adjustment of individual medication corresponding to the marked differences in the functioning of the organism of the various patients (age, sex, body weight, rate of secretion and resorption, problems in bioavailability, etc.); particularly, this is the case in the treatment of prolonged and permanent diseases which may last till the end of life, such as hypertonia and cardiac disorders. For the time being, drugs for this purpose are only available in the form of tablets and injections: of these, the administration of tablets, representing the main part (80–90%) of the medicaments applied in this field, is unsatisfactory owing to difficulties in the adjustment of the proper dosage (breaking or dividing of the tablets to quarters, etc.) as required according to the various rates of resorption, liberation, biological half-life of the drug, due to individual factors.

The essential character of this problem is shown in FIG. 1.; from this the following conclusions can be drawn.

If the conventional form of the drug (i.e. tablet) is administered and the medicament is given twice daily as usual, the steady-state blood level—being of decisive importance in therapy—is highly fluctuating; during a day there may occur periods of 5–6 hours when the concentration of the active ingredient in the serum is below the effective level; just as well there are intervals (2–3 hours) when an extra high serum level can give rise to undesirable side effects (e.g. bradycardia) (●).

A considerable progress is presented in patent EP 0271438, which describes also a tablet, but this is an osmoregulatory system where the release of the active agent from the solid dosage form is diffusion-controlled (see e.g. □, ■). The disadvantages of this preparation are the high cost of production, the difficulty of manufacturing the tablets in a traditionally equipped pharmaceutical factory; finally, the tablet exerts its action throughout 24 hours after swallowing, thus the patient cannot be protected against occasional side effects.

It could be a remarkably better method simply to administer the drug orally in the form of a solution (see, ○) that can also ensure the desired optimal blood level when individually modifying the ordered dosage.

Evidently, the patent of U.S. Pat. No. 4,428,883 started with this consideration suggesting the production of nasal drops containing beta-blocking agents. A serious drawback of this preparation is that the pH value of the solutions is adjusted to nearly neutral (pH=7.4); this is obviously done because, for a longer time, the mucous membrane of the nose can tolerate undamaged only solutions whose pH is near to neutral. However, most beta-blockers undergo hydrolytic decomposition at this pH. Therefore the stability of the system does not comply with the requirements of industrial pharmaceutical production and sanitary considerations.

Unfortunately, most of the patents in this relation deal only with the chemical synthesis or structural modification of beta-blocking agents (DE 3419067 C2; U.S. Pat. No. 3,341,584; DE 3725273 C2; DE 3725273 A1; EP 0339006; U.S. Pat. No. 4,198,526).

We have made comprehensive investigations to study how the presence of polysaccharides and carbohydrate derivatives can modify the passage through the membrane of some of the beta-blocking agents most often used in therapy, this feature being one of the characteristics of absorbability. In our experiments the following types of beta-blocking drugs or their salts were used: oxprenolol, pindolol, sotalol, metoprolol, alprenolol, acebutolol, atenolol, bopindolol, practolol, nadolol and propranolol.

Of the polysaccharides mainly those with variable molecular mass (e.g. 15,000–1,000,000) were used.

It is a known fact than the rate of diffusion of an active agent from a solution will tend to decrease as the viscosity of the system is increased; thereby the passage of the agent through the membrane will be slower.

In the course of the measurements with solutions containing Xanthan Gum (a polysaccharide polymer with beta-1,4-glucan chain) in different concentrations, we found unexpectedly that as the concentration of the auxiliary material was increased (0.001–1.0%), on attaining the value of 0.1% the system was characterised by special and unforeseen properties. For example, in a paradoxical way, the diffusibility of the beta-blocker had a maximum (see FIG. 2. ● - - - ●), and this value corresponded to a higher rate of diffusion than measured for a solution containing no viscosity increasing, stabilising auxiliary material (○ - - - ○).

As the concentration of the auxiliary agent (Xanthan Gum) was further increased, the theoretically expected tendency was restored, i.e. higher viscosity was accompanied by lower diffusibility (□-□).

Human in vivo experiments, based on comparative measurements of the serum levels allowed to draw similar conclusions in every respect (see, Table I), i.e. the highest serum levels were measured at the 0.1% concentration of the auxiliary agent.

Further confirmation is given to the above studies by the fact that when the usual way of administration (drops of solution) is applied, the number of drops (or the mass of the drops) should be reproducible, which is a basic factor in marketing a preparation, particularly one with highly potent action.

It was found also in this respect that when the concentration of Xanthan Gum was varied in the solution, the scattering of the exact number of drops was higher at both below and above 0.1% than at about this particular concentration (see Table II.).

Figure 3A:
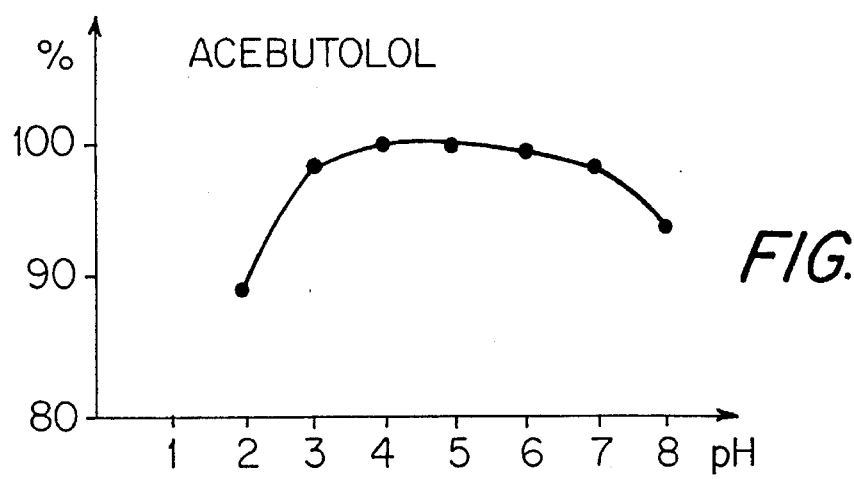
Figure 3B:
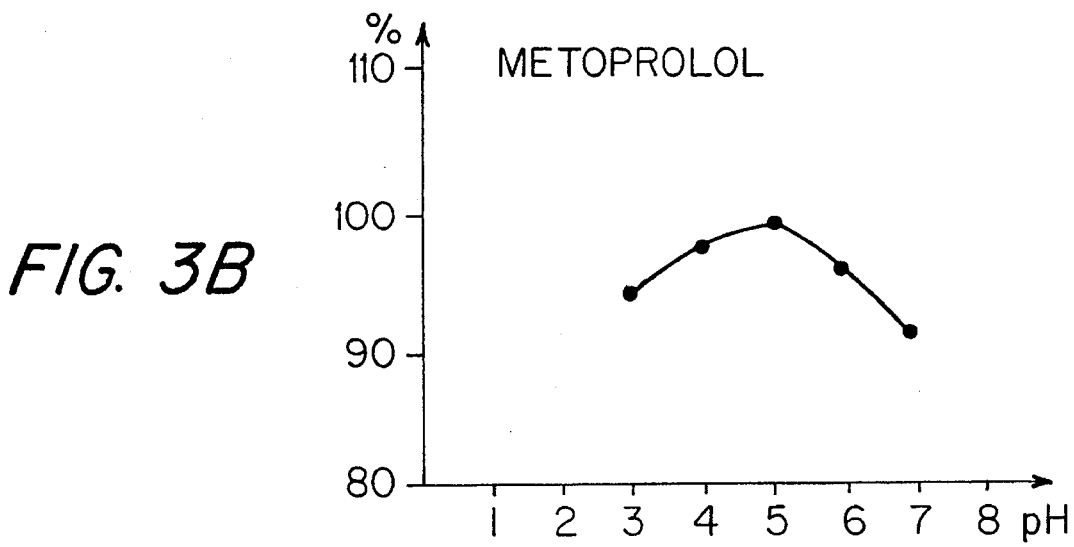
Figure 3C:
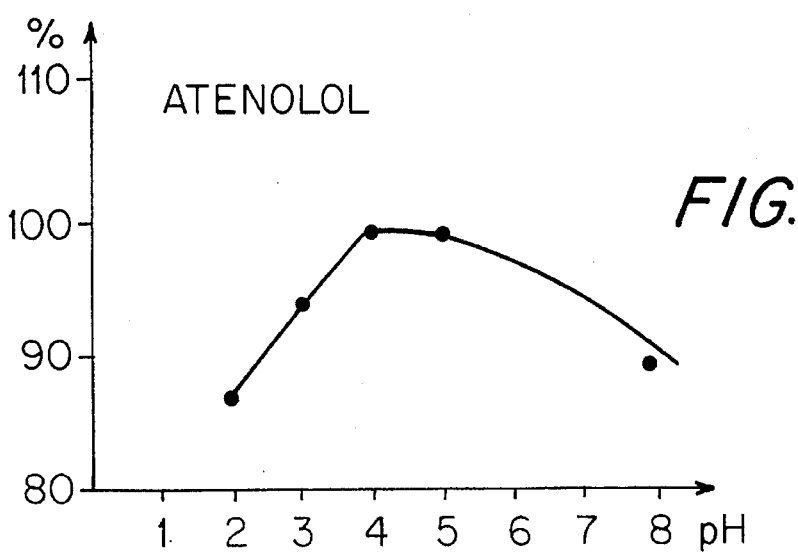

It was another relevant observation than our serial experiments, made partly to study the effect of changing the concentration of the additive and partly that of the pH of the system, revealed that the active agents examined by us had maximal chemical and physical stability at about pH=4, in a solution of 0.1% Xanthan Gum concentration (see FIGS. 3A, 3B and 3C). Rather similar observations were also made in the case of other high-molecular polysaccharide polymers (e.g. dextran, amylodextrin, etc.). This suggested the idea that between some polysaccharide derivatives and certain beta-blockers, within a given interval of concentrations, there is an interaction unknown hitherto, resulting in a better diffusibility, higher stability, and in the possibility of a more exact dosing of the active agent.

The pharmaceutical preparation (oral solutions, drops) developed on the basis of the above principles and observations have the basic therapeutical advantages; allowing the administration of individual dosages; the drug can be given in the form of drops in a convenient and expedient way, which hitherto has not been possible in the therapy of beta-blockers. Other advantages are that the shelf-life of the preparation is very long, the date of expiration can be several years; the carbohydrate component is present at low concentration, e.g., in the case of Xanthan Gum the digestibility of the sugar derivative amounts only to 15%, which is negligible from the aspect of caloric intake or consumption of sugar, thus the drug can also be given to diabetics.

EXAMPLE 1

A buffer solution of pH=4 is made with disodium hydrogenphosphate (dibasic sodium phosphate, $Na_2HPO_4$) and citric acid (Ph.Hg.VII.), and the pH is checked by means of a pH meter. Sorbic acid (0.1 g), dissolved in 95% ethanol (2.0 ml), is added to 70.0 g of the buffer solution. Sodium metabisulphite (sodium pyrosulphite, $Na_2S_2O_5$) is then added and the solution is heated to 80° C. With intensive stirring, 0.1 g of Xanthan Gum (NF XVII) is dissolved in the mixture; after dissolution, stirring is continued for 20 minutes more. The solution is allowed to cool to about 40° C. and then metoprolol tartrate (20.0 g) is dissolved in it, with stirring. Distilled water is added to complete the solution to 100.00 g. The preparation contains 200 mg/g of metoprolol tartrate in a stable, conveniently administrable solution with improved liberation of the active agent.

The preparation is repeated to make a solution in which the amount of Xanthan Gum is 0.01% (w/w).

EXAMPLE 2

The procedure of preparation is the same as described in Example 1, but atenolol hydrochloride (5 g/100 g) is used instead of metoprolol tartrate. The solution thus prepared contains 50 mg/g of atenolol hydrochloride in the form of stable oral drops allowing balanced administration.

The preparation is repeated to make a solution containing 0.01% (w/w) of Xanthan Gum.

EXAMPLE 3

Disodium hydrogen phosphate and citric acid are used to make a buffer solution of pH=2.2, and this value is checked by means of a pH meter. Sodium metabisulphite (0.05 g) is dissolved in 20.0 g of the buffer solution and it is heated to 80° C. Xanthan Gum (0.01 g) is dissolved in the mixture with vigorous stirring which is continued for 20 minutes after complete dissolution. The solution is allowed to cool to 40° C. and pindolol (1.0 g) is dissolved in it with stirring; after dissolution, 80.0 g of propyleneglycol is added. The resulting solution contains 0.01% (w/w) of Xanthan Gum and 10 mg/g of pindolol in a stable, conveniently administrable form.

EXAMPLE 4

The manner of preparing the solution is the same as described in Example 1, but sotalol hydrochloride (16 g/100 g) is used instead of metoprolol tartrate. The resulting solution contains 160 mg/g of sotalol hydrochloride in a stable form which can be administered in a reproducible way.

The procedure is repeated to make a solution with 0.01% (w/w) Xanthan Gum concentration.

EXAMPLE 5

A buffer solution of pH=4 is made with sodium dihydrogen phosphate and citric acid; a pH meter is used to check the correct value. Sorbic acid (0.1 g), dissolved in 95% ethanol (2.0 ml), is added to 70.09 of the buffer, then 0.05 g of sodium metabisulphite is dissolved in it. Dextran (average molecular weight: approx. 60,000) (1.0 g) is dissolved in the solution with stirring, metoprolol tartrate (20.0 g ) is added, and the mixture is stirred to achieve complete dissolution. Finally, the weight of the solution is completed to 100.0 g. During the dissolution of the components warming not exceeding 40° C. may be applied. The resulting solution contains 200 mg/g of metoprolol tartrate in the form of a stable oral preparation.

The procedure is repeated to make a solution containing 0.1% (w/w) of dextran.

EXAMPLE 6

The solution is prepared in the same way of preparing the solution is the same as described in Example 5, but atenolol hydrochloride (5 g/100 g) is used instead of metoprolol tartrate. The stable oral solution contains then 50 mg/g of atenolol hydrochloride.

The procedure is repeated to make a solution containing 0.1% (w/w) of dextran.

EXAMPLE 7

The solution is prepared in the same way as described in Example 1, with the difference that the concentration of Xanthan Gum is to be 0.5% (w/w).

EXAMPLE 8

The manner of preparing the solution is the same as described in Example 5, but the amount of dextran should be now 6.0 g/100 g and pindolol hydrochloride (1.0 g/100 ml) is used instead of metoprolol tartrate. The resulting solution contains 10 mg/g of pindolol hydrochloride.

EXAMPLE 9

The solution is prepared in the same way as described in Example 1, with the difference that the concentration of Xanthan Gum is to be 1.0% (w/w).

EXAMPLE 10

A buffer solution of pH=4 is made with disodium hydrogenphosphate and citric acid, and the correct value is checked by means of a pH meter. Sorbic acid (0.1 g), dissolved in 95% ethanol (2.0 ml), is added to 70.0 g of the buffer. Sodium metabisulphite (0.1 g) is then dissolved in it, and the solution is warmed to 60° C. With vigorous stirring, 2.0 g of amylodextrin is dissolved in the mixture and, after cooling to 40° C., metoprolol tartrate (20.0 g) is added. The active ingredient is dissolved with further stirring and finally the solution is completed with distilled water to 100.0 g.

The procedure of preparation is repeated so that the solution should contain 0.1% (w/w) of amylodextrin.

The solutions contain 200.0 mg/g of metoprolol tartrate.

EXAMPLE 11

The procedure is the same as described in Example 10, but an identical amount of carboxymethylamylum is used instead of amylodextrin.

Using a standard medicine dropper, 10 drops of the medicinal solutions prepared according to Examples 1–11 contain one usual dose of the beta-blocker in a stable form and ensuring reproducible dosage with the required accuracy, the difference by one drop corresponding to a deviation of less than 10%.

TABLE I

Plasma levels of metoprolol in humans after oral administration of 150 mg dose (n = 9; s = ±26.5)

| MATERIAL | TIME | | | |
|---|---|---|---|---|
| | 0.9 | 1.5 | 2.1 | 3.0 |
| | Serum Level (ng/ml) | | | |
| Metoprolol | 7.1 | 420.5 | 482.3 | 350.7 |
| Metoprolol + 0.1% Xanthan | 9.6 | 476.9 | 496.3 | 368.2 |
| Metoprolol + 0.5% Xanthan | 3.6 | 389.3 | 429.6 | 311.7 |

TABLE II

Drop size values of different solutions of β-blockers and xanthan gum as auxiliary material (n = 10, s = standard deviation)

| MATERIAL | CONCENTRATION OF XANTHAN GUM (%) | | | | |
|---|---|---|---|---|---|
| | 0.001 | 0.01 | 0.1 | 0.25 | 0.5 |
| | Average Mass of 10 Drops (g) | | | | |
| Metoprolol 200 mg/ml | $\bar{x} =$ 0.3490 | $\bar{x} =$ 0.3446 | $\bar{x} =$ 0.3301 | $\bar{x} =$ 0.3497 | $\bar{x} =$ 0.3559 |
| | s = 0.0159 | s = 0.0120 | s = 0.0080 | s = 0.0109 | s = 0.0155 |
| Sotalol 160 mg/ml | $\bar{x} =$ 0.3805 | $\bar{x} =$ 0.4067 | $\bar{x} =$ 0.4171 | $\bar{x} =$ 0.4345 | $\bar{x} =$ 0.4052 |
| | s = 0.0158 | s = 0.0180 | s = 0.0173 | s = 0.0220 | s = 0.0086 |
| Atenolol 50 mg/ml | $\bar{x} =$ 0.4038 | $\bar{x} =$ 0.4094 | $\bar{x} =$ 0.4395 | $\bar{x} =$ 0.4604 | $\bar{x} =$ 0.4456 |
| | s = 0.0211 | s = 0.0193 | s = 0.0204 | s = 0.0202 | s = 0.0154 |

In the accompanying Figures, the legends are as follows:

FIG. 1. Simulated plasma concentrations at steady-state of a hypothetical drug with $K_e$=0.3 hr$^{-1}$ and V=1500 mL.

● A 12 mg dose of an oral solution formulation with F=0.7 was given every 12 hours; the simulation was based on Equation 1 with $K_r$=6 hr$^{-1}$ ○ A 2 mg dose of the same oral formulation was given every 2 hours; the simulation was based on Equation 1 with $K_r$=6 hr$^{-1}$ ■ A CR formulation which releases the drug at a zero order rate of 964 ng/hr for a period of 12 hours was given every 12 hours; the simulation was based on Equation 2 with F=0.7

□ A 24 mg dose of a CR formulation which releases the drug with a first order rate constant of 0.06 hr$^{-1}$ was given every 12 hours; the simulation was based on Equation 1 with F=0.7

$$C = \frac{F \times k_r \times D}{V(k_r - k_e)} (e^{-k_e \tau} - e^{-k_r \tau})e^{-k_e(t-\tau)} \quad \text{Eq. 1}$$

$$C = \frac{k_o}{CL_o} [1 - e^{-k_e \tau}] \times e^{-k_e(t-\tau)} \quad \text{Eq. 2}$$

Figure 2:
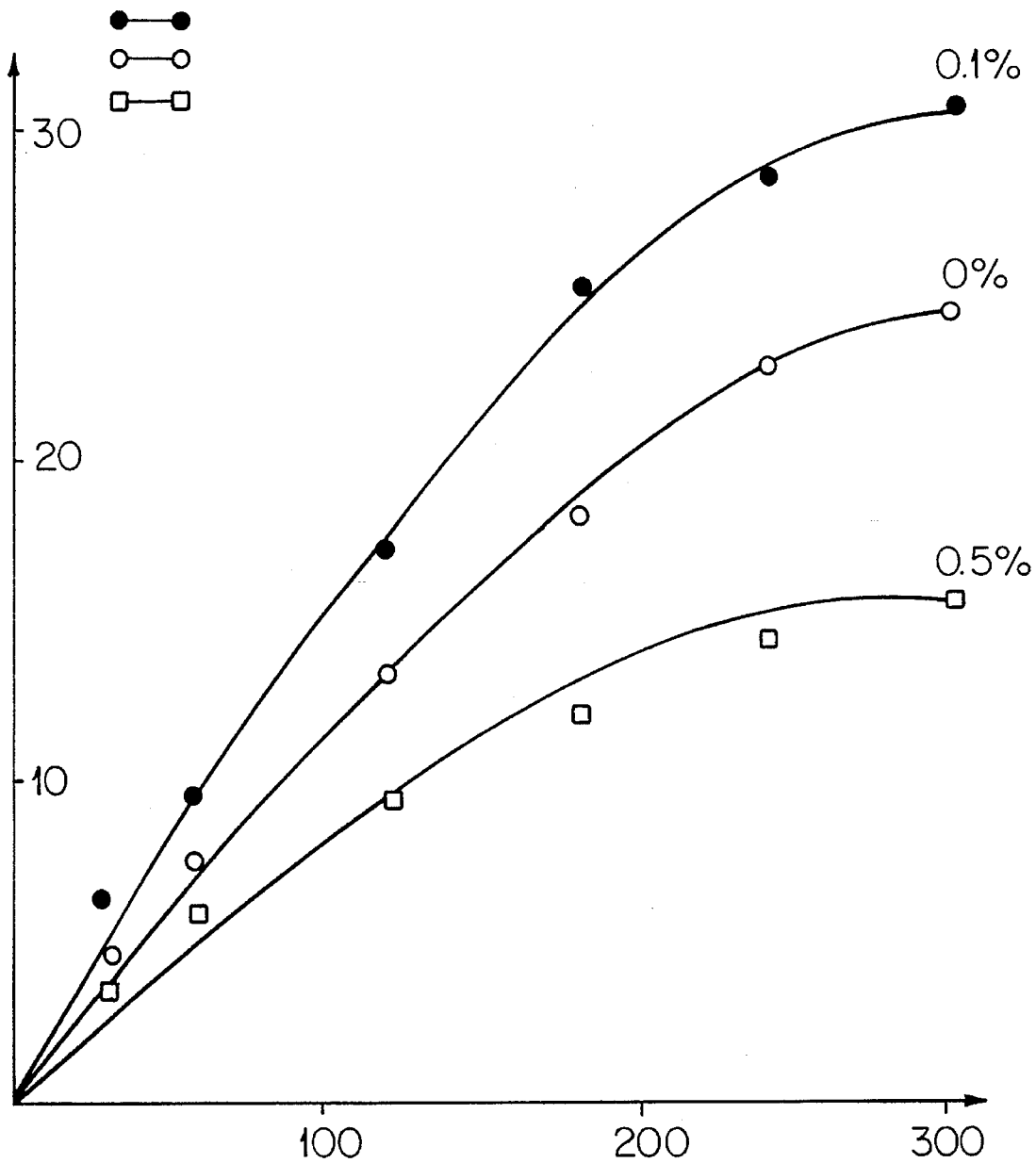

FIG. 2. Diffused percent of metoprolol in vitro as time function (t) in the presence of different concentrations of the auxiliary material using Sartorius Absorption Tester (n=3).

Concentration of auxiliary material

● - - - ● 0.1% Xanthan Gum
○ - - - ○ 0% Xanthan Gum
□ - - - □ 0.5% Xanthan Gum

Donor phase: Buffer pH 6.5
Acceptor phase: Buffer pH 7.5
Membrane: impregnated according to the prescription of Sartorius Co.
Temperature: 39°±1° C.
Active surface of the membrane: 40 cm$^2$ FIGS. 3A, 3B and 3C shown the pH dependence of chemical stability of solutions of metoprolol (FIG. 3B), acebutolol (FIG. 3A) and atenolol (FIG. 3C) solutions stored at 70° C. for one week.

We claim:

1. A process for the production of a stable pharmaceutical for oral administration that provides controlled released of a β-adrenergic blocker active component, which comprises reacting 1 to 20 parts by weight of the β-adrenergic blocker in 100 parts of water with 0.001 to 10 parts of a polysaccharide to obtain a mixture, and adjusting the pH of the mixture to between pH 2 and 4.5 with a buffer.

2. A process according to claim 1, wherein the polysaccharide is a carbohydrate polymer with a β-1,4-glucan chain.

3. A process according to claim 2, wherein the polysaccharide is Xanthan Gum.

4. A process according to claim 1, wherein the temperature of the solution is maintained at about 80° C. for 20 minutes.

5. A process according to claim 1, wherein the buffer is phosphate-citrate, Sörensen, Walpoe, Clark-Lubs, Britton-Robinson or McIlvain.

6. A process according to claim 1, which further comprises adding an antioxidant to the solution.

7. A process according to claim 6, wherein the antioxidant is sodium pyrosulphite or sodium hydrogen sulphite.

8. A process according to claim 1, which further comprises adding a preservative to the solution.

9. A process according to claim 8, wherein the preservative is sorbate or an ester of a phenylcarboxylic acid.

10. A process according to claim 1, wherein the polysaccharide is present in a final concentration of about 0.1% by weight.

11. A process according to claim 1, wherein the polysaccharide is dextran having an average molecular weight of about 60,000 present in an amount of 0.1–0.6 parts by weight.

12. A process according to claim 1, wherein the polysaccharide is amylodextrin present in an amount of 0.1–10 parts by weight.

13. A process according to claim 1, wherein the polysaccharide is carboxymethylamylum present in an amount of 0.1–10 parts by weight.

14. A process according to claim 1, wherein the β-adrenergic blocker is metoprolol tartrate.

15. A process according to claim 1, wherein the β-adrenergic blocker is oxprenolol HCl present in an amount of 0.1–10 parts by weight.

16. A process according to claim 1, wherein the β-adrenergic blocker is pindolol HCl present in an amount of 0.5–1.5 parts by weight.

17. A process according to claim 1, wherein the β-adrenergic blocker is sotalol HCl present in an amount of 1–20 parts by weight.

18. A process according to claim 1, wherein the β-adrenergic blocker is acebutolol HCl present in an amount of 0.5–20 parts by weight.

19. A process according to claim 1, wherein the β-adrenergic blocker is atenolol HCl present in an amount of 1–10 parts by weight.

20. A process according to claim 1, wherein the β-adrenergic blocker is bopindolol HCl present in an amount of 0.1–1 parts by weight.

21. A process according to claim 1, wherein the β-adrenergic blocker is nadolol HCl present in an amount of 1–10 parts by weight.

22. A process according to claim 1, wherein the βadrenergic blocker is alprenolol HCl present in an amount of 0.1–10 parts by weight.

23. A process according to claim 1, wherein the β-adrenergic blocker is propranolol HCl present in an amount of 0.1–10 parts by weight.

24. A process according to claim 1, wherein the polysaccharide has a molecular weight of about 15,000.

25. A pharmaceutical prepared in accordance with claim 1.

* * * * *